(12) United States Patent
Thuliez et al.

(10) Patent No.: US 10,058,429 B2
(45) Date of Patent: Aug. 28, 2018

(54) POLYMER BASED JOINT IMPLANTS AND METHOD OF MANUFACTURE

(71) Applicant: SWISS IDEA BOX SARL, La Neuveville (CH)

(72) Inventors: Jean-Luc Thuliez, Le Landeron (CH); John Nicholas Ayliffe, Ligniéres (CH)

(73) Assignees: Jean-Luc Thuliez, Landeron (CH); John Nicholas Ayliffe, Ligniéres (CH)

( * ) Notice: Subject to any disclaimer, the term of this patent is extended or adjusted under 35 U.S.C. 154(b) by 0 days.

(21) Appl. No.: 14/776,839

(22) PCT Filed: Mar. 14, 2014

(86) PCT No.: PCT/IB2014/000359
§ 371 (c)(1),
(2) Date: Sep. 15, 2015

(87) PCT Pub. No.: WO2014/140773
PCT Pub. Date: Sep. 18, 2014

(65) Prior Publication Data
US 2016/0000570 A1  Jan. 7, 2016
US 2016/0317310 A9  Nov. 3, 2016

Related U.S. Application Data

(60) Provisional application No. 61/787,270, filed on Mar. 15, 2013.

(51) Int. Cl.
*A61F 2/30* (2006.01)
*A61L 27/18* (2006.01)
(Continued)

(52) U.S. Cl.
CPC .......... *A61F 2/30965* (2013.01); *A61F 2/30* (2013.01); *A61F 2/3094* (2013.01); *A61F 2/38* (2013.01);
(Continued)

(58) Field of Classification Search
CPC ...... A61F 2/30965; A61F 27/56; A61F 27/18; A61F 27/303; A61F 27/443; A61F 27/50;
(Continued)

(56) References Cited

U.S. PATENT DOCUMENTS

| | | | |
|---|---|---|---|
| 6,939,569 B1 * | 9/2005 | Green | A61K 9/0036 424/405 |
| 2007/0191946 A1 | 8/2007 | Heinz et al. | |
| 2011/0266265 A1 | 11/2011 | Lang | |
| 2011/0313538 A1 | 12/2011 | Oh et al. | |

(Continued)

FOREIGN PATENT DOCUMENTS

WO  WO 2011/053713 A1  5/2011

OTHER PUBLICATIONS

International patent application No. PCT/IB2014/000359, International Search Report, dated Oct. 14, 2014.

*Primary Examiner* — Moshe Wilensky
(74) *Attorney, Agent, or Firm* — Da Vinci Partners LLC; John Moetteli

(57) ABSTRACT

A method and implant based on injection molding techniques. The method produces polymeric components suitable for implantation with a structure and mechanical properties close to those of natural bone tissue. In a variant, method for making an implant or component thereof includes forming a standard shape foamed blank, and over-molding a thin layer of non-foamed PEEK material onto the standard shaped foamed blank to obtain a final implant component geometry, whereby the blank is completely encapsulated by the over-molded layer.

11 Claims, 15 Drawing Sheets

(51) Int. Cl.
*A61L 27/30* (2006.01)
*A61L 27/44* (2006.01)
*A61L 27/50* (2006.01)
*A61L 27/54* (2006.01)
*A61F 2/38* (2006.01)
*A61L 27/56* (2006.01)

(52) U.S. Cl.
CPC ............ *A61F 2/389* (2013.01); *A61F 2/3859* (2013.01); *A61L 27/18* (2013.01); *A61L 27/303* (2013.01); *A61L 27/443* (2013.01); *A61L 27/50* (2013.01); *A61L 27/54* (2013.01); *A61L 27/56* (2013.01); *A61F 2002/30011* (2013.01); *A61F 2002/30016* (2013.01); *A61F 2002/30624* (2013.01); *A61F 2002/30971* (2013.01); *A61F 2002/3863* (2013.01); *A61F 2310/0058* (2013.01); *A61L 2300/104* (2013.01); *A61L 2430/24* (2013.01)

(58) Field of Classification Search
CPC .. A61F 27/54; A61F 2/30; A61F 2/389; A61F 2/3094; A61F 2/38; A61F 2002/30624; A61F 2002/30016; A61F 2002/3863; A61F 2310/0058; A61F 2300/104
See application file for complete search history.

(56) References Cited

U.S. PATENT DOCUMENTS

2012/0089068 A1* 4/2012 McClure, Jr. ...... A61F 13/00029
602/48

* cited by examiner

POLYMER BASED JOINT IMPLANTS AND METHOD OF MANUFACTURE

CROSS REFERENCE TO RELATED APPLICATIONS

This application is the National Stage of International Application No. PCT/IB2014/000359, filed Mar. 14, 2014, which claims benefit under 35 USC § 119(a), to U.S. provisional patent application Ser. No. 61/787,270, filed Mar. 15, 2013.

COPYRIGHT & LEGAL NOTICE

A portion of the disclosure of this patent document contains material which is subject to copyright protection. The Applicant has no objection to the facsimile reproduction by anyone of the patent document or the patent disclosure as it appears in the Patent and Trademark Office patent file or records, but otherwise reserves all copyright rights whatsoever. Further, no references to third party patents or articles made herein is to be construed as an admission that the present invention is not entitled to antedate such material by virtue of prior invention.

FIELD OF THE INVENTION

This invention relates to an economical method of creating medical implants with a mechanical structure resembling that of natural bone, and to the medical implants themselves, and in particular load bearing joint implants.

BACKGROUND OF THE INVENTION

Presently, implants are usually machined from materials in bulk form, obtained for example from extruded rods or sheets. They may consist of polyethylene (UHMWPe), ceramic or metal alloys such as cobalt-chrome or stainless steel. Material waste is therefore high and may result in excessive costs.

The surfaces of bearings in hip, knee and shoulder implants generally fall into one of the following categories: (1) polyethylene on metal, (2) polyethylene on ceramic, (3) ceramic on ceramic, (4) ceramic on metal, or (5) metal on metal bearings.

Ceramic has the advantage of a very low friction coefficient. It is, however, heavy, relatively expensive and prone to fracture upon impact. In addition, geometric restrictions exist for this family of materials.

Metal alloys, when used in conjunction with polyethylene or ceramic, do function well, but concerns exist about polyethylene wear with a metal alloy counterpart due to the relatively high friction coefficient of this pairing.

Metal on metal bearings are currently causing great concern due to feared release of metal ions. Friction coefficients are relatively high and therefore require post-machining to a level of "super-finishing".

The greatest long-term impact on implant survival is, however, due to polyethylene wear. The literature seems to suggest that the biggest cause of long-term implant loosening and ultimately implant failure is polyethylene wear. When polyethylene debris is released into the joint capsule either due to friction wear or monomer particle release, giant cells called macrophages form around the debris, as the body is not capable of absorbing polyethylene debris. As more macrophages form, the implant can become unstable and fail.

Polyaryl-ether-ether-ketone aka Polyether Ether Ketone Compound (PEEK) is a material renowned for its stability and strength (see for example S. M. Kurtz et al., Biomaterials 28 (32), pp. 4845-4869 (2007), the entire disclosure of which is hereby incorporated by reference). It has one of the lowest friction coefficients when paired with metal alloys. The present 3-phase manufacturing process of polymer synthesis in powder form, granulation in the form of beads, and extrusion into rods or sheets, followed by machining into the required shape, leads, however, to very high costs. PEEK has therefore only been used sparingly in the past.

What is needed is a method of bypassing the costly process of manufacturing for example PEEK implants from bulk material. There is furthermore a need to create implants with a mechanical structure close to that of natural bone. The invention described below solves many of the problems in the art.

SUMMARY OF THE INVENTION

The invention provides a method of processing an implant order which creates a custom implant including several steps. In a first optional step, a variety of polymer or reinforced polymer prosthesis pre-forms are injected in a manner so as to have a dense outer shell resembling cortical bone and a low density core resembling cancellous bone, the pre-form sized so as to allow for secondary machining to a final desired shape without breaking through the dense outer shell into the low density core, the pre-forms thereby having a structure close to that of natural bone and a geometry suited to the needs of a class of patients creating implants with a hollow mechanical structure close to that of natural bone. In a second step, the pre-form which best matches the needs of a particular patient is selected. In a third step, as necessary, the pre-form is machined and finished to better conform to the particular patient. In a fourth step, the pre-form is sterilized. In a fifth step, the pre-form is hermetically packed for delivery of the pre-form to suit the needs of doctor and the particular patient.

In one embodiment of the invention, the plastic is PEEK. In another embodiment, the plastic is "VESTAKEEP"® plastic, available from Evonik Degussa GmbH of Marl, Germany.

It is an object of the invention to produce a variable density, and optionally a hollow (in center) core device which closely replicates the natural bone structure and natural mechanical performances.

It is another object of the invention to produce a flexible device, the elasticity of which is governed by its geometry.

It is yet another object of the invention to produce a device with maximized surface crystallinity and density to mimic cortical bone.

It is yet another object of the invention to produce a bone prosthesis that includes a hollow core with a bactericide gas enclosed inside during production. Diffusion of the gas is adjusted by modulating the crystallinity level of surface layers.

It is a further object of the invention to produce a device with a springiness close to that of the natural biomechanical state and that has a modulus of elasticity very close to that of bone plus excellent toughness and fatigue resistance.

It is another object of the invention to produce a polymeric device in its final form by a one-step process.

It is another object of the invention to produce a polymeric device in a two-step process requiring minimal machining.

In another variant, the invention provides an implant that includes a foamed inner core blank, and an over-molded, non-foamed PEEK layer providing a final implant component geometry.

In yet another variant, the invention includes an implant that features a foamed inner core blank, and an over-molded, non-foamed PEEK layer providing a final implant component geometry.

In yet another aspect, the invention provides an implant (for joints) which includes a foamed and/or non-foamed PEEK substrate, and a diamond like carbon outer layer. The diamond like carbon outer layer is positioned to provide a bearing surface and, the foamed PEEK substrate is located inward of the carbon outer layer. Optionally, the PEEK substrate is reinforced with carbon and/or carbon fibers covering the fiber with a contact layer of DLC.

In yet a further variant, the invention provides a method for making an implant or component thereof that includes forming a standard shape foamed blank, and over-molding a thin layer of non-foamed PEEK material onto the standard shaped foamed blank to obtain a final implant component geometry.

In yet a further aspect, the invention provides a method for making an implant or component thereof comprising: forming a foamed, standard PEEK and/or other load bearing material substrate, and applying a diamond like carbon to the foamed substrate to form a diamond like carbon component of the implant or component thereof. Optionally, a bearing surface is also formed, the bearing surface comprising the diamond like coating, the diamond like coating being outward of the load bearing material substrate. Also, a step of re-enforcing the load bearing material substrate with a carbon containing material is also included. The carbon containing material is a carbon fiber.

These and other aspects of the invention are further described in the drawings, and the detailed description below.

Those skilled in the art will appreciate that elements in the Figures are illustrated for simplicity and clarity and have not necessarily been drawn to scale. For example, dimensions may be exaggerated relative to other elements to help improve understanding of the invention and its embodiments. Furthermore, when the terms 'first', 'second', and the like are used herein, their use is intended for distinguishing between similar elements and not necessarily for describing a sequential or chronological order. Moreover, relative terms like 'front', 'back', 'top' and 'bottom', and the like in the Description and/or in the claims are not necessarily used for describing exclusive relative position. Those skilled in the art will therefore understand that such terms may be interchangeable with other terms, and that the embodiments described herein are capable of operating in other orientations than those explicitly illustrated or otherwise described.

DETAILED DESCRIPTION OF THE PREFERRED EMBODIMENT

The following description is not intended to limit the scope of the invention in any way as they are exemplary in nature, serving to describe the best mode of the invention known the inventors as of the filing date hereof. Consequently, changes may be made in the arrangement and/or function of any of the elements described in the exemplary embodiments disclosed herein without departing from the spirit and scope of the invention.

Thus, whereas the following description applies to the specific example of a tibial insert for a total knee replacement, the method can equally be applied to all kinds of orthopedic, cardio, neuro or any other implantable or non-implantable medical devices. Other examples are acetabular cup inserts for total hip replacement, and glenoid implants for total shoulder replacement, spinal implants, trauma implants.

All these devices have a number of features in common, such as a variable-density body with a wear resistant, dense outer surface, a porosity decreasing from the center towards the outer surface, and a springiness dominated by geometry rather than the elastic modulus of the base material.

Figure 1:
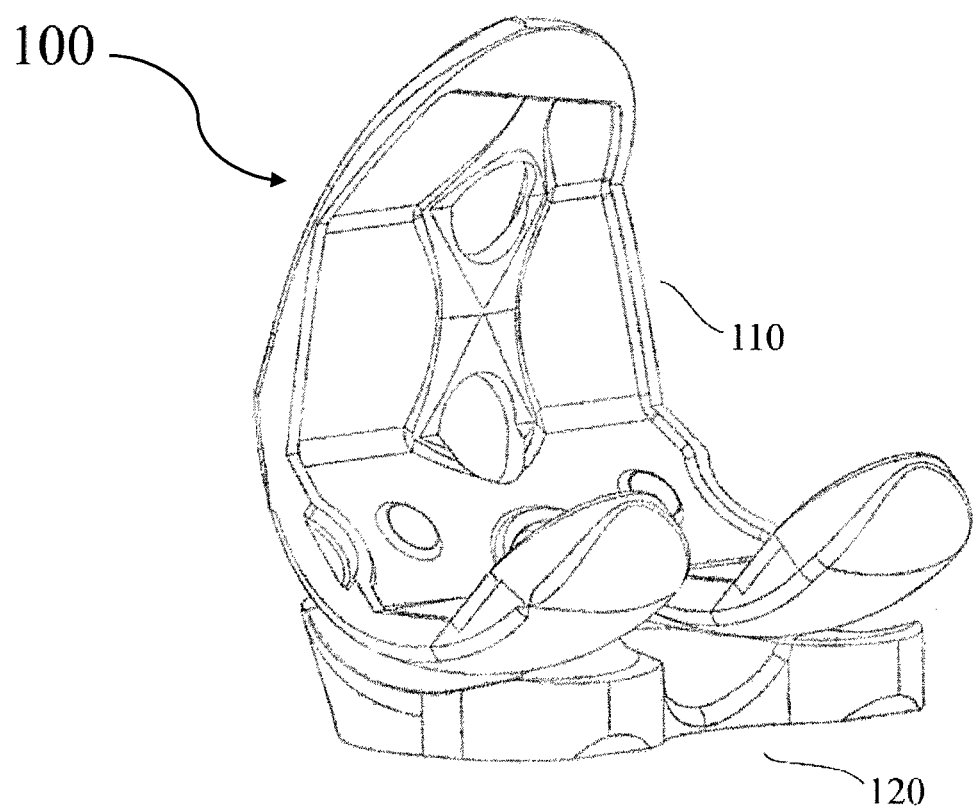
FIG. 1 is a perspective view of a polymeric tibial plateau underneath a metallic condyle.

Referring now to FIG. 1, an exemplary application of a polymeric implant 100 is tibial plateau 120 located underneath metallic condyle 110. The polymeric implant is created via the processes described below. The device 200 itself is shown in the perspective view of FIG. 2. In the preferred embodiment, device 200 is manufactured by injection molding in a single step in one variant of the invention. Injecting to the final device geometry has the advantage of minimal waste generation and improved performance by means of excellent surface finish, while avoiding the need of any post-injection machining. Key to the injection process is furthermore the capability of forming a variable density structure offered by different gas injection molding processes. The device geometry is tailored to the specific anatomical needs of the particular patient who undergoes a joint replacement procedure. Devices 100, 200 are sized and dimensioned to match the patient's native joints so as to provide proper fit and function mimicking the native joint, on the prosthetic side of the replacement and matching the non-prosthetic side of the patient. The gas is preferably an inert gas, such as nitrogen. Because water is essentially incompressible, water injection is not preferred.

Figure 3A:
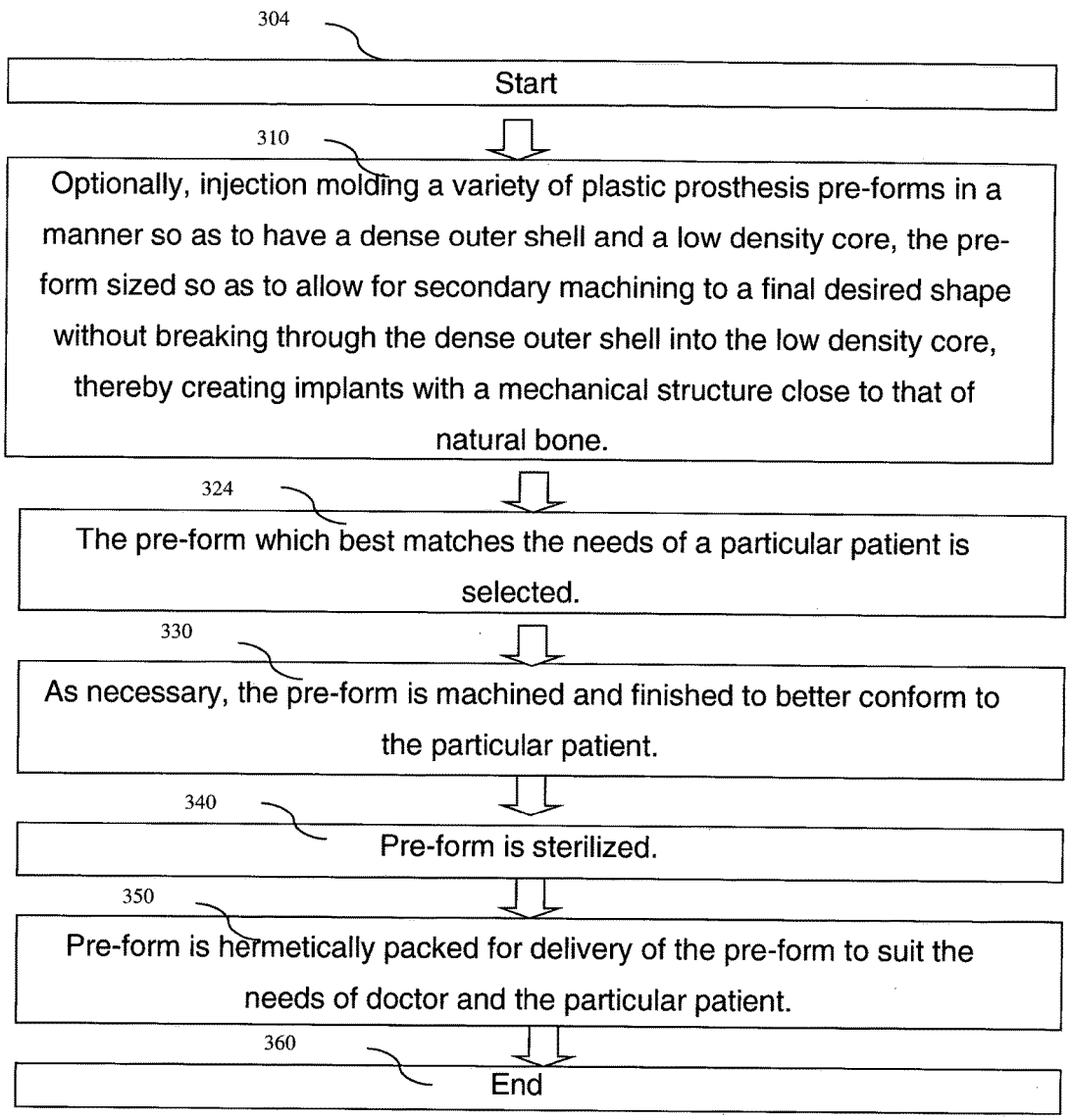
FIG. 3A is a flow chart of the method of the invention.

Referring now to FIG. 3A, the method of processing an implant order 304 starts such that it creates a custom implant including several steps. In a first optional step 310, a variety of plastic prosthesis pre-forms are injection molded in a manner so as to have a dense outer shell resembling cortical bone and a low density core resembling cancellous bone, the pre-form is sized so as to allow for secondary machining to a final desired shape without breaking through the dense outer shell into the low density core, the pre-forms thereby having a structure close to that of natural bone and a geometry suited to the needs of a class of patients creating implants with a mechanical structure close to that of natural bone. In a second step 324, the pre-form which best matches the needs of a particular patient is selected. In a third step 330, as necessary, the pre-form is machined and finished to better conform to the particular patient. In a fourth step 340, the pre-form is sterilized. In a fifth step 350, the pre-form is hermetically packed for delivery of the pre-form to suit the needs of doctor and the particular patient. It is appreciated that one or more of the method steps are incorporated in application software which run on the systems described in the present invention. The application software automates one or more of the steps via algorithms. The Algorithms have functionality for analysing imaging scans, e.g. MRI and x-ray scans of native joint geometry, size and composition, to re-create custom joint prosthesis anatomical replacements for the native joint being replaced. The replacement joint components are also created in another variant of the invention using 3-D printing systems. In this manner, a prosthesis is created that matches or substantially matches the native joint components being replaced.

In one embodiment of the invention, the polymer used in the implant of the present invention is PEEK. In another embodiment, the polymer is "VESTAKEEP"® plastic, commercially available from Evonik Degussa GmbH of Marl, Germany. In another embodiment, the polymer PEEK is SOLIVA® plastic, commercially available from SOLVAY Belgium.

In another embodiment, the pre-form is formed so as to have a desired density for the same external geometry. In another embodiment, the pre-form is formed so as to have a desired stiffness for the same external geometry. In another embodiment, the pre-form is formed to have a highly crystallised surface thereby allowing significant reductions in friction coefficient with a paired material. In another embodiment, the pre-form is formed to minimize material use while maintaining required characteristics.

In yet another embodiment, an anti-infection agent, such as silver ions or silver nitrates, are injected or integrated into the plastic used to form the pre-form during production of the pre-form.

In another aspect of the invention, a pre-form prosthesis is provided, having a dense outer shell and a low density core, the pre-form sized so as to allow for secondary machining to a final desired shape without breaking through the dense outer shell, the pre-forms having a structure close to that of natural bone and a geometry suited to the needs of a class of patients.

The pre-form has an external configuration suitable for a first class of patients and an outer shell having a thickness so as to extend to a depth into the outer shell at which a suitable external surface can be formed by secondary machining while leaving a wall thickness allowing a prosthesis machined from the pre-form to suit a second class of patients. The first class is a largest size class of patients and the second class is a smallest size class of patients, thereby allowing a single pre-form to suit anticipated needs of most patients.

Gas assisted molding is a preferred process suitable to the fabrication of the bone-like prosthesis of the invention. Information about this process is available in *Mod. Plast. Int.* 19, No. 2, February 1989, entitled GAS-ASSIST INJECTION MOLDING: MORE VARIANTS FROM MORE SOURCES, by Mapleston P., the content of which is incorporated herein by reference and relied upon. A suitable injection molding machine is available from Engel AG, of Schwertberg, Austria. Working with Bauer Kompressoren of Munich, Germany, Engel AG produces a module which simplifies the application of gas injection technology, including leakage monitoring. A suitable "ENGEL gasmelt" unit is made up on a compressor, a pressure accumulator, and a pressure control module. This injection molding machine alerts the system operator as soon as predefined limit values are exceeded and is integrated in the CC 200 control unit of the ENGEL injection molding machine, enabling an operator to monitor the entire process (including the gas supply) via the display on the machine control unit.

Another method introduces a porogen agent mix with polymer to form gas. In this known technique, PEEK polymer is mixed with a porogen agent before introducing mix in the machine (with the expansion agent degrading around 300°). When the temperature of 300° is reached in the screw of the injection molding machine, porogen agent will start to degrade thereby creating gas ($CO_2$ for example). This degradation expansion takes place in the cavity of the mold under temperature (elevated). When the temperature returns back to an ambient temperature, the expansion of the gas is stopped or halted.

Still another technique involves direct gas introduction. The equipment and process involved is described in publications of the manufacturers, Teledyne ISCO of Lincoln, Nebr., and KraussMaffei Technologies GmbH of Munich, Germany (describing their "cellform" technology), described below.

Figure 3B:
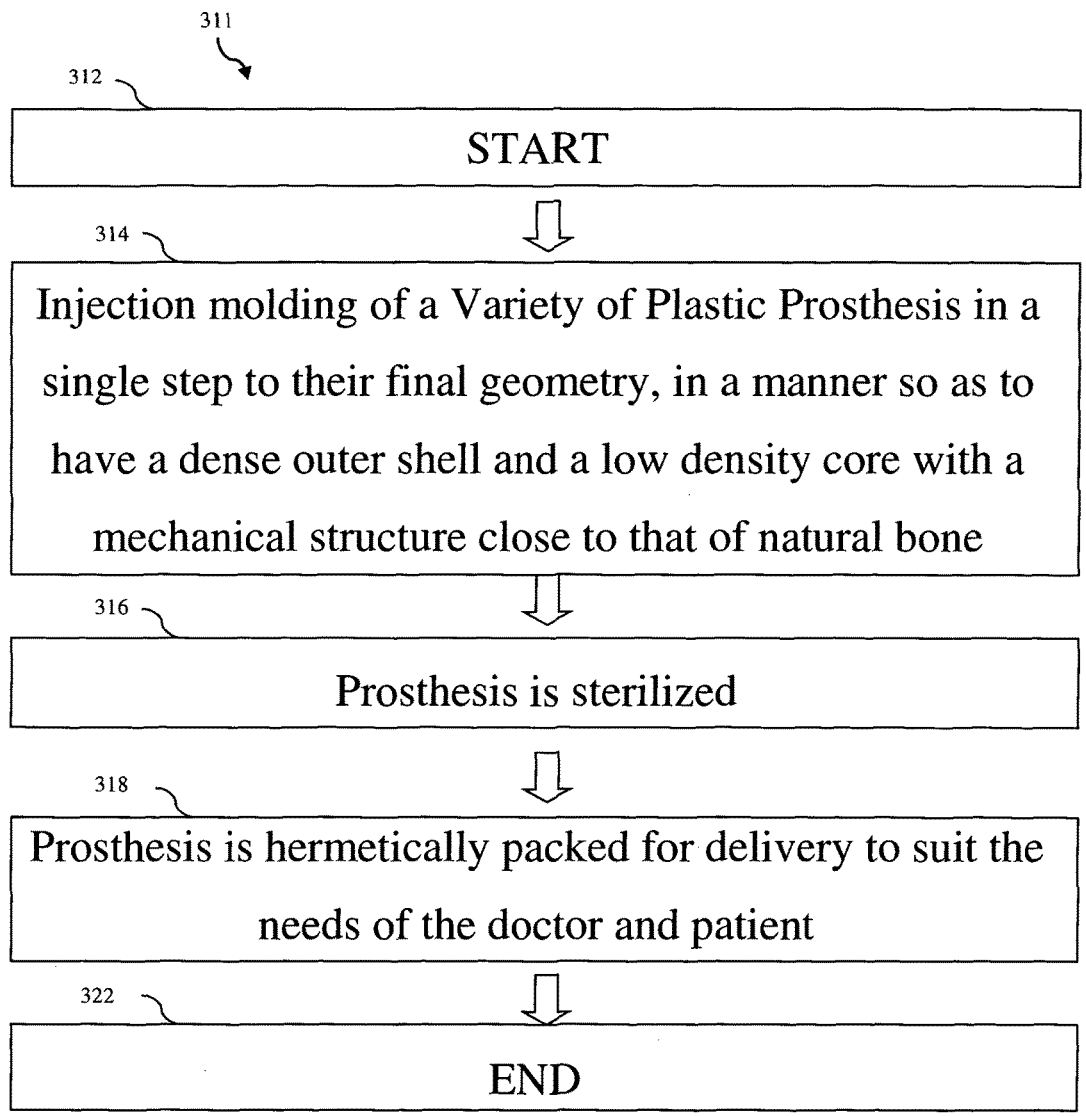
FIG. 3B is a flow chart of another method of the invention.

Now referring to FIG. 3B, a method 311 and application software provides functionality to the systems described herein that incorporates one or more the method steps. Step 312 indicates the start function. Step 314 involves actuating the injection molding of a variety of plastic prosthesis components in one or more steps to obtain their final geometry in a manner so as to have a dense outer shell and a low density core. This mechanical structure mimics that of the natural bone of the patient, and is custom designed in one variant of the invention so that the real time bone structure of the patient and the prosthesis is matched or substantially matched. In step 316, the prosthesis is sterilized. In step 318, the prosthesis is hermetically packed for delivery to suit the needs of the doctor and patient. Step 322 indicates the end of the operation.

Figure 3C:
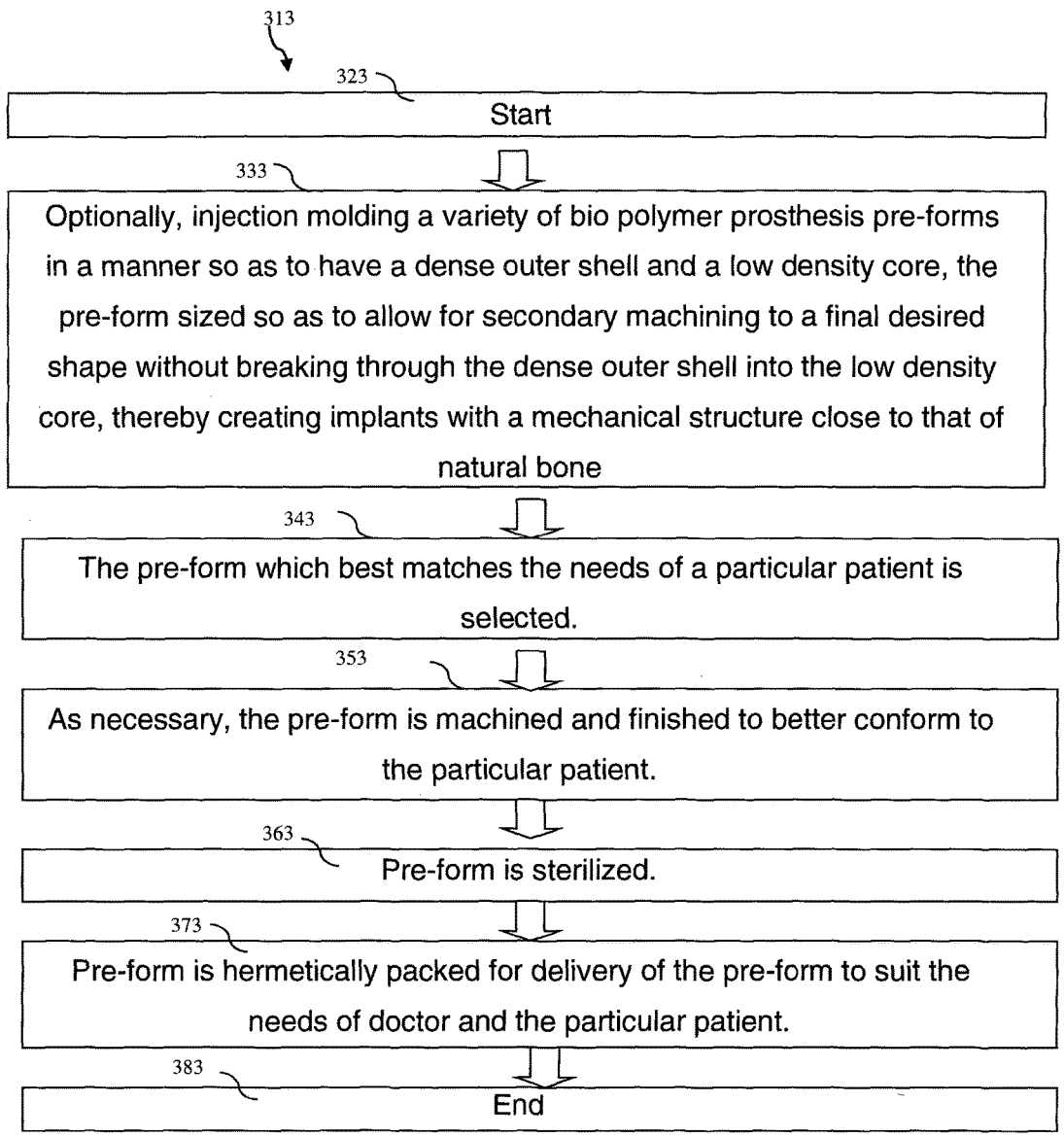
FIG. 3C is a flow chart of the variant of the method of the invention.
Figure 4:
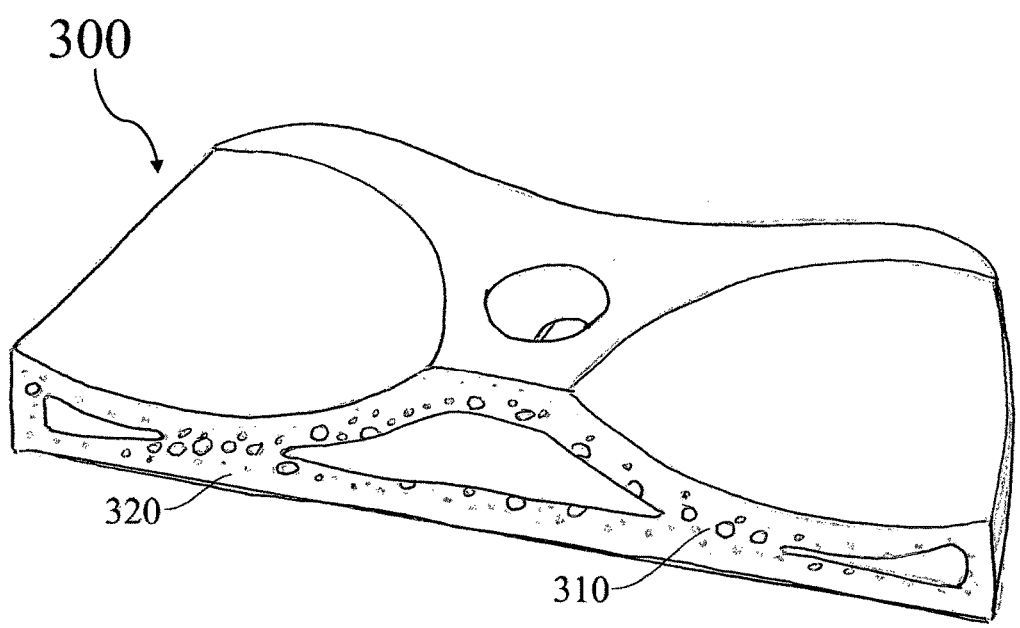
FIG. 4 is a perspective view of a cross-section of a polymeric tibial plateau.
Figure 5:
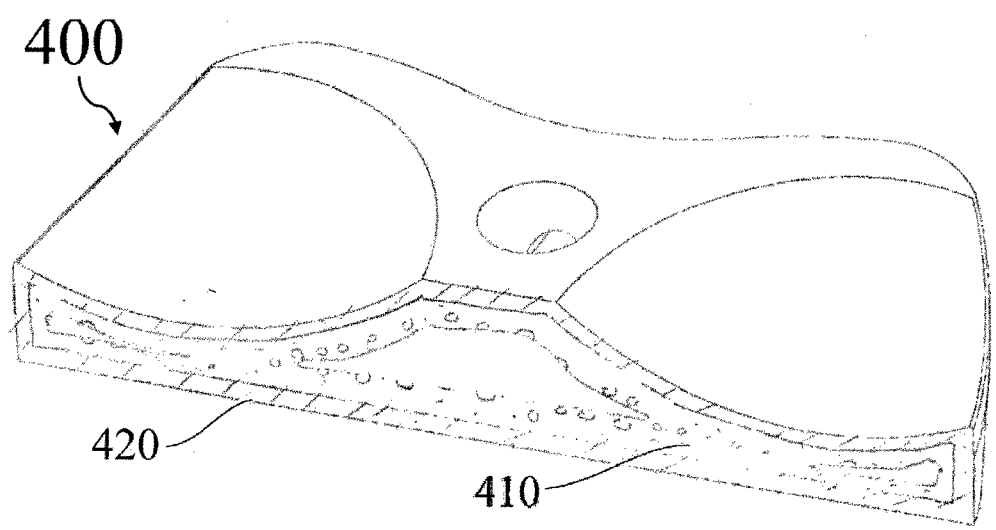
FIG. 5 is a perspective view of a cross-section of a polymeric tibial plateau before the final machining step.

Now referring to FIG. 3C which illustrates application software and method 313 in which the application software actuates one or more of the method steps on the systems described herein. The method and the application software include functionality so that start step 323 is executed. Step 333 follows which optionally actuates system components for injection molding of a variety of bio polymer prosthesis pre-forms in a manner so as to have a dense outer shell and a low density core, the pre-form sized so as to allow for secondary machining to a final desired shape without breaking through the dense outer shell into the low density core, thereby creating implants with a mechanical structure close to that of natural bone. Step 343 selects the pre-form which best matches the needs of a particular patient is selected. Step 353 actuates the system so that components of the system machine and finish the pre-form to better conform to the particular patient. In step 363, the pre-form is sterilized. In step 373, Pre-form is hermetically packed for delivery of the pre-form to suit the needs of doctor and the particular patient. Step 383 indicates the end of the process and application programme functionality.

The variable density results from the injection of a decomposing agent along with the polymer pellets into the mold. The reaction of this agent with the polymer pellets slightly below the fusion temperature of the polymer causes the latter to foam. Referring now to FIG. 3A, the porosity 310, 320 of 300 increases more and more towards its center by gas bubble formation, resulting in an increase of polymer density towards its outer surface.

In addition, slow cooling in the injection molding tool produces an extremely hard surface of the device. The variable density polymer thus mimics the biomechanics and structure of bone tissue, with a hard outer surface resembling wear resistant cortical bone, and a less dense, sponge-like structured or porous interior similar to cancellous bone. Its density, stiffness and elasticity can be tailored according to the needs of specific applications. The crystallization of the surface region of the polymeric component induced by slow cooling furthermore improves its friction coefficient when paired with the other elements of the complete device, for example made of metal alloy or ceramic. This reduces both the risk of wear debris and monomeric particle release.

Among the polymers with foam forming properties PEEK is the one most favoured according to the invention. In another particular embodiment, the plastic is "VESTA-KEEP"® plastic, available from Evonik Degussa GmbH of Marl, Germany may be used. There exists a version with a standard melt powder—Vestakeep I4P and a version with flowable granulate—Vestakeep I2G. A white version for tooth replacement is Vestakeep MC4420G.

Figure 2:
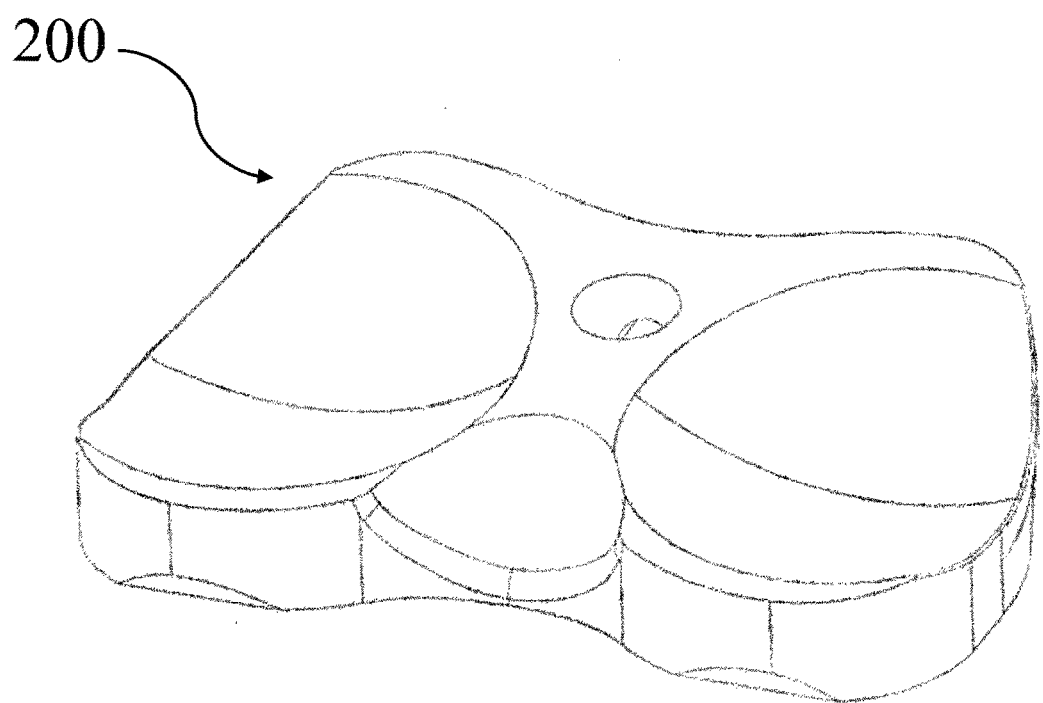
FIG. 2 is a perspective view of a polymeric tibial plateau.

In another embodiment the device is manufactured in a two-step process in which high pressure injection is first used to shape a polymer into a structure similar to that of FIG. 2, albeit somewhat larger in size. After slow cooling causing again crystallization and hardening of the surface, this component, called a "pre-form" is then removed from the molding tool and stored until subject to the second step, wherein the structure receives its final geometry by machining. Referring now to FIG. 3C, just a few mm of the outer skin of pre-form 400 need to be removed in the machining step to arrive at an exact copy of device 200, resulting again in small material waste.

Figure 6:
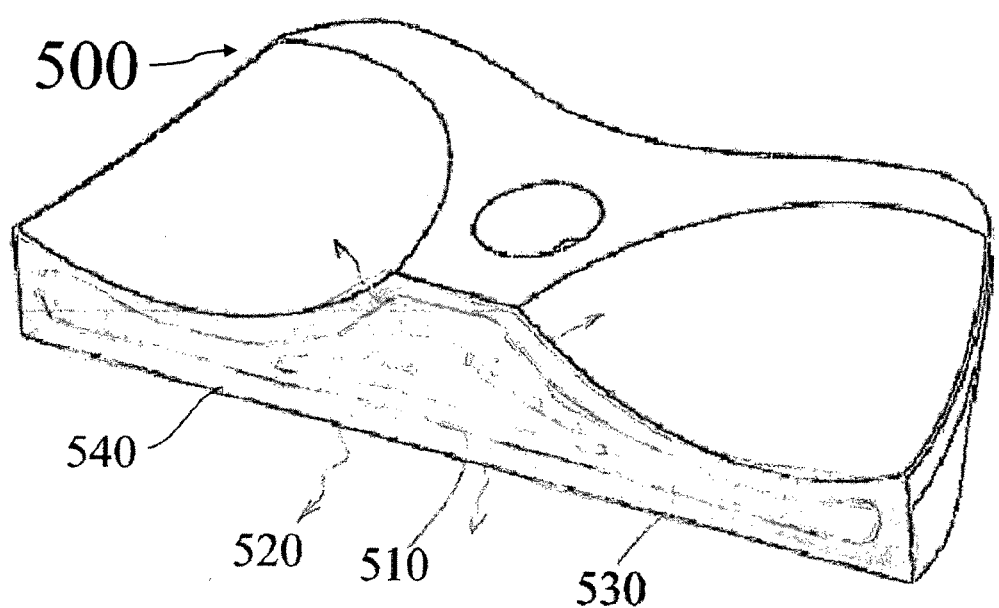
FIG. 6 is a perspective view of a cross-section of a polymeric tibial plateau during the injection of fluid or gas.
Figure 7:
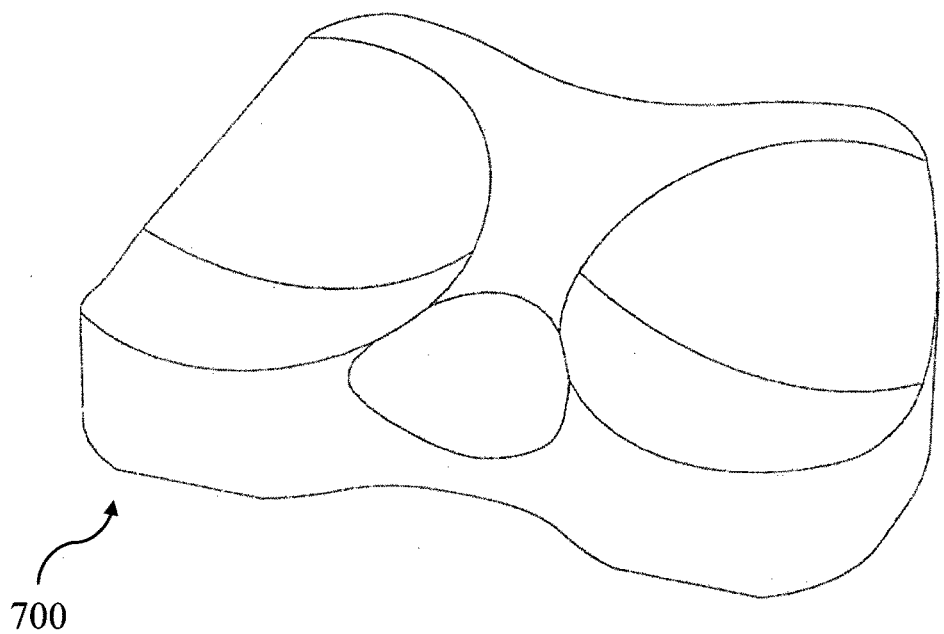
FIG. 7 is a perspective view of another variant of the components of an implant of the present invention.

Referring now to FIG. 6, gas or fluid injection into the core 510 of the device, or its generation therein, can be augmented by an anti-infection agent, such as silver in ion form. Silver nitrate, in powder form, may be mixed with PEEK pellets prior to heating and entry in the injection screw.

The gas will diffuse 520 through the external walls 540 of the device post-implantation and over a certain period of time. The anti-infection agent reduces the risk of infection and the short-term rejection of the device by the patient.

It is understood that the geometry and design of the hollow structure of the device will add elasticity, making it more flexible, beyond what is expected from the elasticity modulus of the base material. The flexibility and springiness of the device is in fact close to the natural biomechanical state. The improved load transmission causes thus additional comfort to the patient.

The level of stiffness can furthermore be tailored by controlling the foaming process, the injected material and the geometry of the device. It is therefore possible to imagine stiffer, less forgiving devices or flexible, more forgiving devices, depending on implant type (spine, hip, knee, etc.) or patient criteria such as age or activity level.

Use of a small amount of superior quality polymer to produce the final geometry or pre-form makes the vs/hole device less costly. Less material is used as the injected shape is either the final geometry or very close (pre-form). Less material is also used when density is decreased towards the core of the device through the foaming process. A pre-form close to the final shape and size finally greatly reduces the need of secondary machining, again reducing costs.

Finally, it is worth mentioning that the thermal history according to the invention is limited to the synthesis of the polymer (powder), granulation (beads) and injection—solidification/crystallisation. This final step in the thermal history of the injected device (final geometry or pre-form) allows for three-dimensional crystallisation during the curing process in the molding tool. The curing time is adjustable by adjusting cooling times and temperatures in the cavity.

As described herein a variety of different methods for foaming processes are used to create the implant, systems and components thereof. In one variant, the "Gasmelt" in-cavity process described below are used. It is appreciated that other commercially available processes of gas introduction in the injection screw as well as additive foaming material added to the base resin "pre-injection" are also used herein in the methods described. It is further appreciated that although PEEK is the current preferred high-performance polymer used herein, in another variant of the invention, any polymer which can be foamed is used in the method of creating an implant described herein. In another variant of the invention, memory shape materials are used as substrates in the present invention. These include Zeniva™ PEEK resin, Proniva™ self-reinforced polyphenylene, and Veriva (t) polyphenlysulfone (PPSU), Eviva™ polysulfone, commercially available from Solvay Speciality Polymers USA, LLC (4500 McGinnis Ferry Road, Alpharetta, Ga. 30005-3914 USA (www.solvay.com)), and is a part of Solvay's line of Solvira™ Biomaterials. In yet another variant, Altera™ PEEK polymer materials (e.g. and other PEEK shape memory materials) are also used in the implant of the present invention. These PEEK materials are available from MedShape, Inc., 1575 Northside Drive, NW, Suite 440, Atlanta, Ga. 30318, USA.

In yet another variant of the invention, a variety of accessories are used with the bone implant or joint replacement prosthesis of the present invention, which combined with the implants described herein form kits for native bone joint and other tissue replacement. These include suture anchor implants, by way of example, from GoG Sports Medicine, commercially available from Orland Park, Ill. USA, as well as those commercially available from MedShape, Inc., 1575 Northside Drive, NW, Suite 440, Atlanta, Ga. 30318, USA. The implants and/or accessories described herein are used in a method that includes bone joint prosthesis implantation as well as processes that aid in re-attaching soft tissue to a prepared bone surface using a variant of kit accessories that include PEEK material suture anchors. It is appreciated that the kit accessories and implant provide the benefit of radiolucences when elements of the kit are used in vivo in the patient.

In other variants of the invention, other bone implants and prosthesis further are created using the methods described herein and comprising the combinations of materials and layers described herein. These include, by way of example, cranial bone implants, spinal implants, long bone implants, wrist implants, foot bone implants, ankle implants, and of course various other bone joint implants. In yet other variants of the invention, non-load bearing implants are also created using methods described herein. These include implantable hearing systems, e.g. for moderate to severe sensorineural hearing loss, and the like. These hearing devices and methods use the natural ear drum and an implant created using the methods and kits described herein. The hearing devices, systems and kits operate by stimulating the cochlea with a prosthetic stimulator. These implants include fully implantable implants and also partially implantable hearing aids by way of example.

In yet another variant any silver containing compound is also used in the implant and hip implant method of creation. Furthermore, barium sulphate is also included in the method and implant with other additives to provide a radio-opaque material. This additive is used either alone, or in combination, with silver oxide (anti-infection compounds).

In yet another variant of the invention, the method for making an implant includes the following steps: 1. Overmolding step. As a variation to going to final geometry in one step, a standard shape foamed blank (not necessarily in PEEK but still using the foaming methods described earlier) is formed, which is then over-molded with a thin layer of (non-foamed) PEEK to arrive at a final implant component geometry.

In yet another variant of the invention, the method includes applying a diamond like carbon (DLC) (http://www.diamondcoating.net/) to a foamed PEEK substrate in order to have a bearing surface comprising: a. a foamed PEEK component coated with DLC and b. a foamed PEEK or standard PEEK or "other" bearing material component inwards of the DLC coated surface. This DLC coated component can also cover an interior that is reinforced with carbon or carbon fibers.

DLC is an acronym for diamond-like carbon or non-naturally occurring diamond. As the name implies, diamond-like carbon has some of the valuable properties of diamond. It can be applied as a coating on almost any material that is compatible with the vacuum in which it is usually produced. When applied in pure form it is as hard as natural diamond or can be made even harder. In pure form these diamond coatings offer extraordinary protection against abrasive wear and attack from atmospheric moisture and chemical vapors. Although smooth when seen with visible light, diamond like carbon actually has the form of a cobblestone street. There are two different crystalline geometries for diamond. "Common" diamond known from jewelry has carbon atoms arranged in 3-dimensional cubic lattices. In a rare form called lonsdaleite the lattice would be hexagonal, like cells in a beehive. In DLC the cobbles are not crystalline; they are amorphous because they are made from random alternations between cubic and hexagonal lattices. The cobbles have no long-range order and so they have no fracture planes along which to break. The result is a very strong material. By stacking more and more layers of these nodules, DLC coatings can be made that at the same time are amorphous, flexible, and yet purely 3-dimensionally ($sp^3$) bonded "diamond". The hardest, strongest, and slickest is known as tetrahedral amorphous carbon, orta-C. For example a coating of only 2 μm thickness of ta-C increases the resistance of common (ie. type 304) stainless steel against abrasive wear; changing its lifetime in such service from one week to 85 years. Such ta-C can be considered to be the "pure" form of DLC, since it consists only of $sp^3$ bonded carbon atoms. Fillers such as hydrogen, graphitic $sp^2$ carbon, and metals are often used in 6 other known forms of "impure" DLC to reduce production expenses. Such economies decrease the service lifetimes of the articles being coated; sometimes by drastic amounts.

Implantable PEEK Carbon Used in the Implant Components Examples

Implantable-grade PEEK polymer, which is suitable for long-term (greater than 30 days) implantation, shows significant benefits over traditional materials, such as polyethylene, metallic alloys, and ceramics. Similarly, compression tests after soaking in physiological saline for up to 5000 hours have confirmed the stability of the polymer under these exposure conditions.

Carbon-Fiber Compounds Used in the Implant Components

Short-fiber-reinforced materials are produced by combining carbon fibers with the polymer in a twin-screw compound extruder under controlled conditions suited to medical polymer production. The resulting compound may be injection molded using a system with process temperature capability approaching 400° C. Typical fiber loading may be 30-35% by weight for short-fiber compounds, increasing the material's modulus from 3.5 to approximately 18 GPa and its tensile strength from 100 to 230 MPa. With a stiffness close to that of cortical bone, carbon-fiber-reinforced implantable-grade PEEK polymer compounds are used in applications for which stress shielding may have a critical effect on the lifespan of an implant. For example, if an implant is manufactured from metallic components with a significantly higher stiffness than cortical bone, the higher stiffness may lead to bone resorption and weakening at the implant site as the device sustains a greater proportion of the applied load.

Polyetheretherketone (PEEK) polymer is an exceptionally strong engineering thermoplastic that retains its mechanical properties even at very high temperatures. The material is tough and abrasion resistant with high-impact strength and excellent flexural and tensile properties. It has a low coefficient of friction and resists attack by a wide range of organic and inorganic chemicals and solvents. Implantable-grade PEEK polymer, which is suitable for long-term (greater than 30 days) implantation, shows significant benefits over traditional materials, such as polyethylenes, metallic alloys, and ceramics. Because of its unique properties, implantable-grade PEEK polymer is used in a variety of components.

Implantable-grade PEEK polymer is characterized by its biocompatibility—the suitability of a material for exposure to the body or bodily fluids, and its biostability—the ability of a material to maintain its physical and chemical integrity after implantation in living tissue. The combination of strength, stiffness, and toughness, along with the ability to be repeatedly sterilized without the degradation of its mechanical properties, makes it suitable for the implant described herein.

Traditionally, metals or ceramics are chosen for hard-tissue applications, and polymeric materials are selected for soft-tissue applications. One of the major problems in orthopedic surgery is the mismatch of stiffness between the bone and metallic or ceramic implant. The moduli of metals and ceramics are fixed at their inherently high levels, whereas the modulus of implantable-grade PEEK can be adapted.

This adaptability reduces stress concentrations that can be transferred to the bone and stimulates the healing process. Bone remodeling occurs in response to physical stress, or lack thereof. Bone is deposited in sites that are subject to stress and resorbed from areas where there is little stress. The method and implants described herein solve these problems.

Implantable-grade PEEK polymer is one of the most chemically resistant polymers available. It displays chemical resistance, confirmed by 30-day exposure to simulated body fluid environments utilizing a sodium chloride solution, glycerol, vegetable oil, and an alcohol, with no adverse influence on the material's mechanical properties. Similarly, compression tests after soaking in physiological saline for up to 5000 hours have confirmed the stability of the polymer under these exposure conditions. The natural unfilled polymer is characterized by high strength, extreme resistance to hydrolysis, and resistance to ionizing radiation. Therefore, it can be repeatedly sterilized using conventional gamma irradiation, steam, or ethylene oxide. It has been exposed for 2500 hours at 200° C. to 14-bar steam without significant deterioration of its mechanical properties. Its chemical structure makes it very tolerant to gamma irradiation. In contrast, gamma irradiation of other polymeric materials induces cross-linking or chain scission, which leads to weakening and enbrittlement.

The material's chemical structure ensures extreme stability against hydrolysis, even at elevated temperatures. The relative thermal index (or continuous VSE temperature) against VL 746 B for PEEK is 260° C. Implantable-grade PEEK polymer can be steam sterilized repeatedly without reduction or deterioration in mechanical properties. In addition, EtO residues are within the limits specified in ISO 10993-7, even following three repeated sterilization cycles.

Manufacturing Processes and Biocompatibility Testing for Implants or Implantable Components The development of implantable-grade PEEK polymer has been achieved using enhanced manufacturing procedures, supported by physical, chemical, and mechanical testing conducted at key stages of production. The material is manufactured to the highest level of purity, with complete material history traceability in the process described herein.

Formulation with Additives Used in Implant Components

Implantable-grade PEEK polymer compounds can be formulated using a variety of additives including carbon fibers, barium sulphate, and glass fibers. The additives satisfy various application-specific requirements. Glass fibers may be compounded with the polymer to enhance its mechanical properties without substantially changing the color of the base material. Because the polymer is naturally radiolucent, adding barium sulphate at varying concentrations enables the x-ray density of devices to be tailored from mild to strong radio-opacity. By compounding implantable-grade PEEK polymer with short carbon fibers, the strength of the natural unfilled polymer can be increased significantly. With higher strength, the polymers can address higher-stress applications.

Carbon-Fiber Compounds Used in Implant Components

Short-fiber-reinforced materials are produced by combining carbon fibers with the polymer in a twin-screw compound extruder under controlled conditions suited to medical polymer production. The resulting compound may be injection molded using a system with process temperature capability approaching 400° C. Typical fiber loading may be 30-35% by weight for short-fiber compounds, increasing the material's modulus from 3.5 to approximately 18 GPa and its tensile strength from 100 to 230 MPa. With a stiffness close to that of cortical bone, carbon-fiber-reinforced implantable-grade PEEK polymer compounds are used in applications for which stress shielding may have a critical effect on the lifespan of an implant. For example, if an implant is manufactured from metallic components with a significantly higher stiffness than cortical bone, the higher stiffness may lead to bone resorption and weakening at the implant site as the device sustains a greater proportion of the applied load. This example is in contrast to implant components made from implantable-grade carbon-filled PEEK compounds that demonstrate elastic properties similar to the surrounding bone and that reduce the effects of stress shielding.

Carbon-Fiber Composites Used in Implant Components

Implantable-grade PEEK polymer may be used as the matrix polymer in combination with continuous carbon fibers to form reinforced composite materials. This fiber reinforcement significantly enhances the mechanical properties of the polymer. In one example, continuous-fiber-reinforced implantable-grade PEEK polymer is made using a proprietary pultrusion process in which carbon fibers and PEEK are processed into a filament, brought together into bundles, and shaped into a rod. For a continuous-fiber material in pultruded rod form, the fiber loading is approximately 70% by weight (60-62% by volume), which significantly increases the mechanical properties of the material in the fiber direction. Flexural strength is increased from approximately 150 to more than 1000 MPa, and stiffness is increased from 3.5 to 150 GPa.

The mechanical properties of continuous-fiber-reinforced rod products are comparable to those of metallic materials such as cobalt-chrome, titanium, alloys, and stainless steel. Such composites are also available as preimpregnated tapes, comprising uniaxially aligned carbon fibers and a PEEK matrix. The tapes are used for hand lay-up compression-molded or filament-wound parts. Components, or successive plies of reinforcing materials, or resin-impregnated reinforcements are applied to the mold and the composite is built up by hand. Compression molding then cures the material.

Fiber Reinforcement in the Implant Components

Continuous-fiber-reinforced PEEK rods by composite flow molding are used to make load-bearing structural components and fastening elements in the present invention, in one variant. The use of composite flow molding significantly improves implants by reducing operation trauma, shorten in-patient hospital stays, increase patient comfort, enable less-invasive applications, and increase tissue tolerance. Aside from mechanical properties that compare favorably with metals, implantable-grade PEEK polymer composites offer superior medical imaging compatibility under magnetic resonance imaging (MRI). They are radiolucent, meaning they are almost invisible under x-ray inspection, allowing uncluttered image visualization. Traditional metallic implants are not radiolucent, which prevents a complete inspection of tissue and bone.

Carbon-Fiber Reinforcement Used in the Implant Components

Adding short carbon fibers to implantable-grade PEEK polymer increases its tribological wear properties. Tribology, or how a material interacts with the surface of another material while in motion, is a critical concern in the development of orthopedic implants, because such implants need to retain their structure while moving against other surfaces and components. The selection of an alternative bearing surface may change how a joint is affixed to the bone, or it may lead to structural consequences in terms of stiffness and load transfer to the bone. Implantable-grade PEEK has a very strong bond with carbon fibers so fiber release is significantly reduced or eliminated. Additionally, because of its creep resistance, implantable-grade PEEK polymer can sustain comparatively large stresses over long periods of time without significant time-induced extension, and with good fiber-matrix interfacial bond strength.

Wear Debris Reduction for Implants

In addition to linear wear rates, the size, shape, and number of wear particles also affect the life of an implant, and are decreased using the methods and implant designs described herein. When micron-sized wear particles are released into the surrounding tissues, the macrophage cells are provoked, resulting in osteolysis (the dissolution or degeneration of bone tissue) and possible implant loosening. Osteolysis tends to become evident during the second decade of an implant's lifespan. While it is claimed that highly cross-linked polyethylene may afford lower wear rates, simulator studies indicate that the wear debris may be slightly smaller, resulting in a greater number of wear particles per year. The short history of the current cross-linked polyethylene implants precludes a conclusion regarding the potential for osteolysis.

Simulator tests indicate that acetabular inserts made from implantable-grade PEEK polymer with optional carbon fibers yield lower wear rates and a smaller amount of wear particles compared with other materials. The particles were biologically tested and results showed that the material was well tolerated biologically. Implantable-grade PEEK polymer particles extracted from the simulator test for acetabular inserts were found to be smaller than 15 µm. The particles were biologically tested in concentrations of 0.5 and 1.0 mg/ml with human fibroblasts. These tests showed that the material was well tolerated biologically.

Implant Design Solutions

In addition to benefiting from the mechanical, chemical, and biological characteristics of implantable-grade PEEK, the polymer is used because of the varied design solutions it provides.

The polymer may be processed using conventional thermoplastic processing equipment and techniques such as injection molding, extrusion, compression molding, and powder coating as described in the examples herein. It is used in injection molding operations to economically mass-produce high-performance components without the need for postprocess annealing or machining. Extrusion may be used to produce film and sheet and monofilament tubing, rods, and compounds with pigments or fillers. The viscosities of these materials are comparable to commodity polymers at their melt temperatures. Implantable-grade PEEK polymer is available in three grades: standard viscosity, medium viscosity, and low viscosity.

Implantable-grade PEEK polymer possesses a unique combination of biocompatibility, x-ray and computed tomography translucency, and MRI compatibility. Furthermore, its adjustable mechanical performance, chemical resistance, sterilization options, and ability to be thermally processed easily make this thermoplastic an increasingly popular choice for implantable devices. The following reference is incorporated into this specification in its entirety: http://www.mddionline.com/article/using-implantable-grade-peek-vivo-devices Injection Foamed PEEK Used to Create the Implant An exemplary PEEK thermoplastic used in the invention is commercially available from Victrex® plc and Zotefoams plc (Zotefoams plc, 675 Mitcham Road, Croydon, Surrey CR9 3AL England), and includes Victrex® PEEK™ high performance engineering thermoplastic, with densities as low as 650 kg/m3 or lower. The process uses Zotefoams' nitrogen saturation technology to impregnate granules, which can then be used in conventional injection molding equipment to produce foamed parts or in extrusion to produce continuous foam profiles. The foams maintain many of the properties of the initial polymer such as outstanding chemical resistance, low flammability, high temperature performance, good dielectric performance and excellent radiation resistance, combined with light weight, in-built buoyancy and improved thermal insulation. The following reference is incorporated into this specification in its entirety: http://www.zotefoams.com/pages/en/whats-new-read.asp?ID=8. The following reference is also incorporated into this specification in its entirety: PEEK BIO-MATERIALS HANDBOOK, http://books.google.ch/books?id=zrMxVjc8qSMC&pg=PA183&lpg=PA183&dq=injection+foamed+peek&source=bl&ots=AMcT8txNgY&sig=UUWKKJgb4Sfp30FQ9QtbxIwKkrI&hl=fr&sa=X&ei=maYDU4-6IOqqyAOl34CYBQ&ved=0CHQQ6AEwCQ#v=onepage&q=injection%20foamed%20peek&f=false.

Molecular Injection Molding Process Used to Create the Implant Example

Microcellular injection molding is also used in the process of the present invention, in one variant. The following reference is incorporated into this specification in its entirety and describes one such process: Microcellular Injection molding, Par Jingyi Xu, expansion gas for PEEK, http://books.google.ch/books?id=10LlsingyRUC&pg=PT142&lpg=PT142&dq=injection+foamed+peek&source=bl&ots=6DUcBASAA8&sig=_lgeqONbt_0IW3lfPzFjCfx_O30&hl=fr&sa=X&ei=maYDU4-6IOqqyAOl34CYBO&ved=0CEYQ6AEwAw#v=onepage&q=injection%20foamed%20peek&f=false.

Structural Foam Processes Used to Create the Implant Examples

Several structural foams created by commercially available processes are used in the process to create an implant of the present invention. These include by way of example processes to create the materials used in the invention:
 1) FOAMMELT Structural Foam,
 2) ENGEL FOAMMELT Structural Foam Mucell™ with gas introduction in a barrel,
 3) GASMELT/WATERMELT processes,
 4) STANDART PROCESSES (NEEDLE),
 5) BLOWOUT PROCESSES,
 6) LOCAL GAS INJECTION PROCESSES,
 7) MULTIPOINT INJECTION PROCESSES, and
 8) WATERMELT CIRCULATION PROCESSES.

By way of example, foam injection molding is used to create an implant described herein. Foam injection molding is an extension of conventional extension molding with foaming. Commercially available systems include Teledyne Isco Syringe Pumps commercially available from Teledyne Isco Inc., 4700 Superior St, Lincoln, Nebr. 68504, USA. Such systems include structural foam molding systems which include positive displacement pumps, accumulators between the extrusion barrel and the shut-off valves. Another example of systems used to create the implant include CellForm™ systems for creating foam processes for injection molding under the brand Trexel SCF systems commercially available from Krauss Maffei Group, Krauss Maddei Strasse, Munich, Germany (www.krausemaffei.com). These systems provide for homogeneous distribution of blowing agents as a result of the screw design in their systems. See, e.g. FIG. 8.

Figure 8:
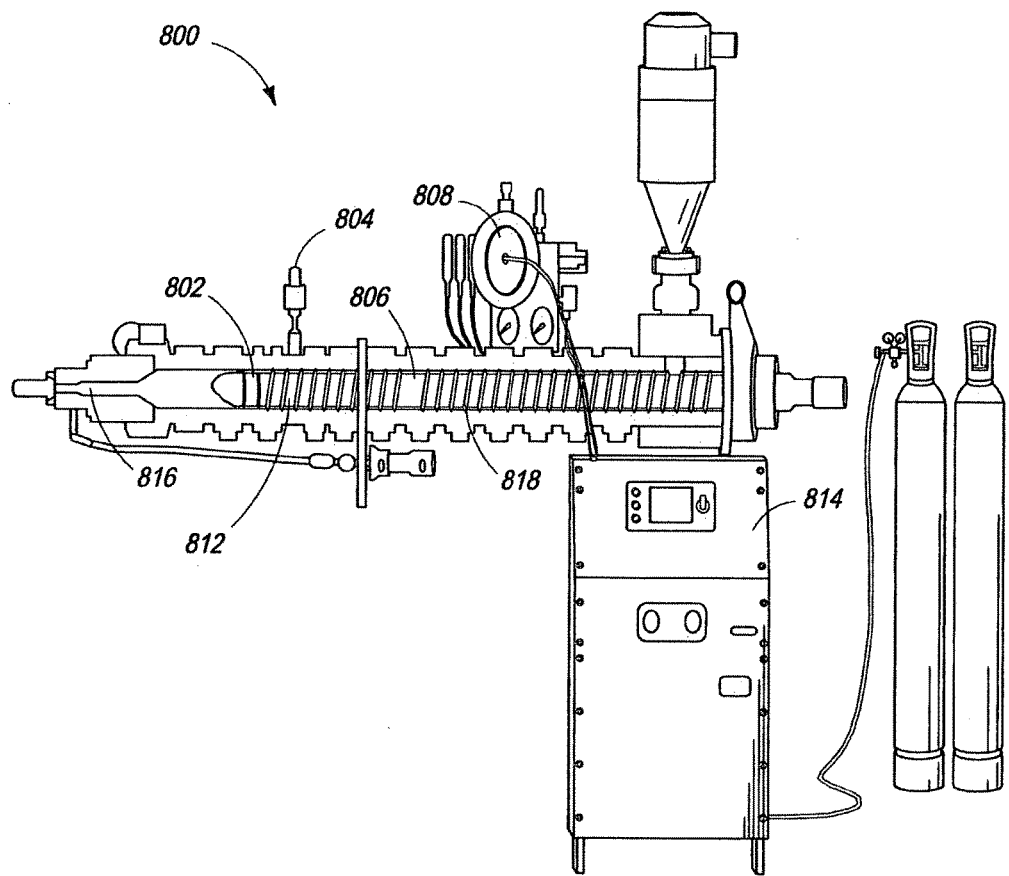
FIG. 8 is a schematic of a system used to create an implant of the present invention.

Now referring to FIG. 8, a system 800 used by and controlled with the application software described herein is illustrated to create the implant system and components thereof. This is an example of the type of system used in the process described herein but of course other commercially available systems are also described herein. System 800 includes a front end return valve 802 in line with and SCF injection system 804. Back end return valve 806 is located downstream as is SCF interlace kit 808, and SCF metering system 814. Upstream of front end return valve 802 is the SCF is completely dissolved in the polymer melt at point 816. At or near the SCF injector 804 is location SCF injection system 812, and in back of the back non-return valve 806, the plasticizing of the polymer melt occurs at point 818. The system is further controlled by the SCF metering system 814. FIG. 8 describes one process used with the method and application software running on the system described herein.

In another variant of the process and application software running and controlling the system(s) described herein, the ENGEL™ gasmelt with gas introduction into the cavity utilizes a portion of a preferred method executed on the commercially available systems described herein. Another variant of at least part of the process and system used in the present invention is commercially available from Engel Austria GmbH of Schwertberg, Austria. The Engel gasmelt and watermelt processes and systems commercially offered by ENGEL permit the molding of parts with thicker walls and sections than normally permitted by the material used. With both processes, a separate medium is injected into the mold during the mold filling operation. This medium generates pressure inside the part so as to ensure that the shrinkage of the material which normally occurs during the cooling phase cannot pull the surfaces of the parts away from the walls of the mold cavity and cause sink marks and other surface blemishes. The pressure medium used is either nitrogen or water. Nitrogen is used in cases where chemical inertness is a prime consideration; water is used in cases where cycle time, heat transfer and long melt flow-paths take priority. Other additives as described herein are also introduced into the process. The pressure media do not just serve to compensate shrinkage but also, and equally importantly, to reduce wall thickness by producing hollow areas inside the parts, yet desired non-hollow and smooth, strong outer surfaces. Reducing wall thickness also reduces the amount of material used, and this in turn means a reduction in cooling time.

In the Gasmelt or Watermelt processes, application software on the system 8000 or other systems creates a mold cavity that is first partially filled with a defined quantity of melt, followed by controlled injection at a pressure of between about 30 and 400 bar or 20 and 200 bar respectively. Of course, other pressures are also used herein. The pressure medium forces the melt against the walls of the mold cavity in order to mold the part. Injection of the pressure medium is effected either via the machine nozzle (only if gas is used) or via a nozzle located near the gate or via a nozzle leading directly into the mold (gas and water). The medium cannot enter the mold until its pressure exceeds that of the melt. After control of the molding function with the application software and system described herein, the pressure medium takes over the holding pressure function normally performed by the controlled injection unit. Upon completion of the defined holding pressure phase, most of the pressure medium—water or gas—is reclaimed for use during the next molding cycle. The method used herein and controlled by the application software includes at least 4 process stages. In stage 1, the injection unit with shut-off nozzle is in a closed position. Melt accumulates in the space in front of the screw in readiness for injection. In stage 2, the shut-off nozzle opens. Melt is injected (partial filling), then the shut-off nozzle closes. In Stage 3, gas is injected via the gas needle into the mold cavity. The nitrogen expands inside the melt and forces the latter against the walls of the mold cavity (the optimum quantity of melt is determined beforehand by successive approximation). In stage 4, gas pressure is maintained during the cooling phase (the gas pressure performs the holding pressure function. Gas pressure is then reduced and the gas is reclaimed. The part is then demolded. Of course it is understood that additional process steps and stages of additive introduction and finishing of the implant component are introduced in this basic outline of this process as described herein.

In yet another variant of the invention described herein microcellular foam structures through uniformly dispersed nitrogen are formed utilizing the methods, system and control application software described herein to create an implant, e.g. a hip implant. The mechanical foaming process uses an adapted plasticizing cylinder, in which nitrogen or carbon dioxide are injected during the plasticizing process and are firmly dispersed by the homogenizing action of the screw. The high pressure in the plasticizing cylinder causes the gas to dissolve in the melt completely. Not until the melt is injected into the mold does the gas expand to form foam. The advantage of the extremely even distribution of gas in the melt lies in the consistently high quality and dimensional stability of the molded implant component. Shrinkage and warpage are minimized in the implant component. Weight savings of between 25 to 30% and cycle time reductions of up to 50 percent are also provided. The process includes one or more of the combination of process stages controlled by the system components and application software described herein, with or without the introduction of additional additive stages and/or finishing steps. In stage 1, the plasticizing process takes place after injection of the previous shot and during the mold cooling phase. With the needle valve nozzle closed, the melt builds up in the space in front of the screw. Gas injections introduce nitrogen in its supercritical fluid state into the metering zone during the plasticizing process. Under the heat and pressure generated by the plasticizing screw, the gas is completely dissolved and dispersed in the melt. In stage 2, the mold opens and the part is demolded. The meld for the next shot is kept under pressure so as to have a uniform melt temperature. This is a prerequisite for the optimally uniform foam structure of the molded part. In stage 3, the mold closes. The needle valve nozzle opens and the meld is injected. During injections, the finely dispersed gas in the melt nucleates and expands to produce a microcellular foam. The foamed melt flows easily, retaining a relatively low mold locking force. In stage 4, the melt expands to fill the mold, forming a solid outer skin amid a microcellular foam core of extremely uniform structure.

In another variant of the process a chemically blown foam is created using the systems and methods, and application software described herein. With the chemically blown foam process, the gas is generated by the chemical decomposition of the blowing agent consisting of chemical substances when exposed to the heat of the melt during the plasticizing process. A powdered blowing agent is mixed into the molding compound together with an adhesive oil. As the pressure of the gas in the meld is extremely low, only very low injection pressure is used for the mold filling process.

In yet another variant of the process, a mechanically blown foam is created using the systems and methods, and application software described herein. The mechanically blown foam is produced by introducing pressurized nitrogen or carbon dioxide directly into the melt during the plasticizing process. The high pressure in the plasticizing cylinder causes the gas to dissolve in the melt completely, thus ensuring its uniform dispersion. Following injection of the gas laden melt into the unpressurized mold, the gas and the melt separate, whereby the gas expands to produce the microcellular foam. With this process, the pressure of the gas in the melt is considerably higher than that generated by the chemical foaming process, thus permitting a wider processing latitude and greater molding precision. The process permits lightweight precision components of implants from engineering polymers with desired wall and section thicknesses, and provides faster cycle times. Within a defined pressure and temperature range, nitrogen becomes a "super-critical fluid" which dissolves the melt completely during the plasticizing process. The melt and the gas separate again following injection of the melt into the mold cavity. This creates a desired cross-section of the structural foam molded component of the implant, and there is a sandwiched structure formed by the solid outer skin and the foamed core. There is further a reduction of cavity pressure through increased degrees of foaming, and a saving of material, and time for creation of the implant component.

In another variant, the PEEK™ compounds used herein are commercially available from Performance Plastics, Inc., 4435 Brownway Avenue, Cincinnati, Ohio 45209 USA are also used herein to create the implant and components thereof described herein. These include, by way of example, unfilled compounds, glass filled compounds, and carbon filled compounds. In yet other variants, Vestakeep™ PEEK polymers are used to create the implant of the present invention. These polymers are commercially available from Evonik Degussa GmbH, 45764, Marl, Germany. In another variant and optionally, PEEK biomaterials used in the implant described in Kurtz, et al. PEEK Biomaterials in Trauma, Orthopedic and Spinal Implants, Biomaterials, 2007 November, 28(32); 4845-4869 which is incorporated by reference herein as if fully set forth. Various chemical blowing agents for foaming thermoplastics are also used in the processes for creating the implant described herein. By way of example, Palmarole™ EXP 141/16, Palmarole™ EXP 141/185, Palmarole™ EXP 141/175 are used herein. They are commercially available from Adeka Palmarole, Espace 103, 103 rue de Strasbourg, 68300 Saint-Louis, France (www.adeka-palmarole.com).

Figure 9:
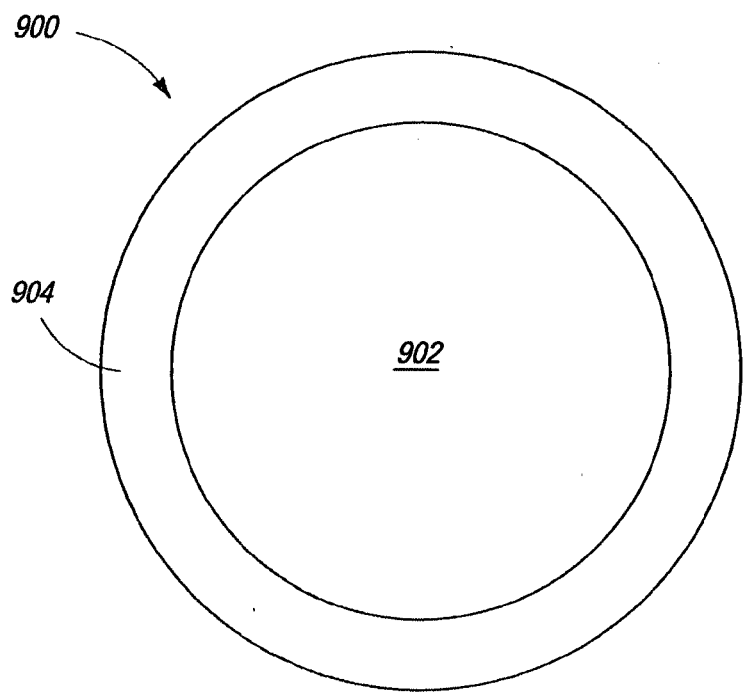
FIG. 9 is a schematic cross-section of an implant of the present invention.
Figure 10:
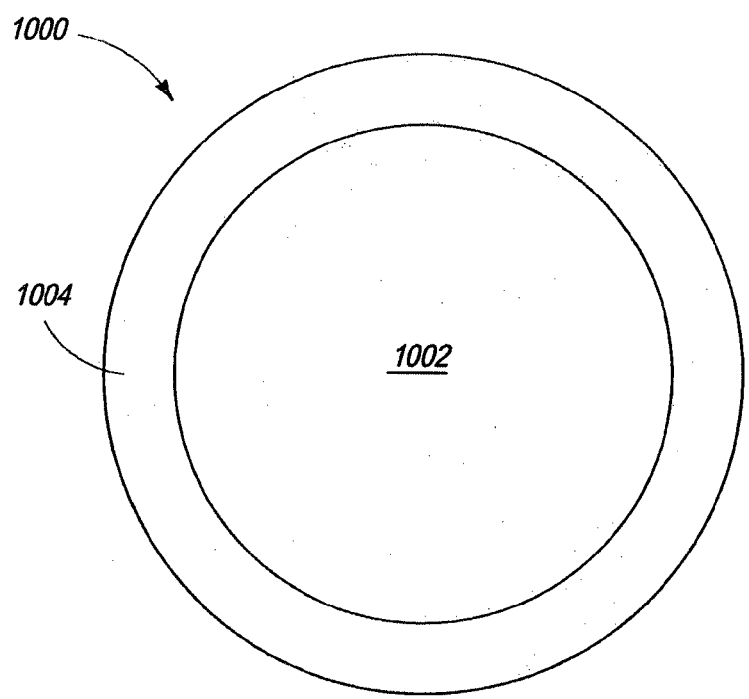
FIG. 10 is a schematic cross-section of an implant of the present invention of a variant of FIG. 9.

Now referring to FIG. 9, a cross section of a component of an implant 900 that includes a foamed inner core blank 902, and an over-molded, non-foamed PEEK layer 904 providing a final implant component geometry is illustrated. In a variant as shown in FIG. 10, implant 1000 can optionally include a foamed and/or non-foamed PEEK substrate 1002, and a diamond like carbon outer layer 1004. The diamond like carbon outer layer 1004 is positioned to provide a bearing surface and, the foamed PEEK substrate 1002 is located inward of the carbon outer layer 1004. Optionally, the PEEK substrate 1002 is reinforced with carbon and/or carbon fibers. It is appreciated that the layers 904, 1004 can have a different density than the layers 902, 1002. It is appreciated that the density of layers 904, 1004 can be higher or lower than that of substrates 902, 1002 so that they mimic the natural density distribution between layers of natural bone, generally, or to match those of a particular patient. It is appreciated that a more natural prosthesis is thus created to the patient's native bone structure In another variant of the invention, the DLC layers do not cover all of the substrate and/or totally encapsulate the substrate. The DLC single or multiple layers are partially applied and a partial coating exists over the substrate, e.g. only covering targeted areas of the components where there is a bearing surface.

In yet a further variant, the DLC layers are applied to: a. a foamed substrate, b. a non-foamed substrate, c. and/or a foamed "sub-substrate" with a non-foamed outer layer, or a combination thereof, It is appreciated that the sub-substrate and/or substrate can include one or more of a combination of a.)-c.) described above.

Figure 11:
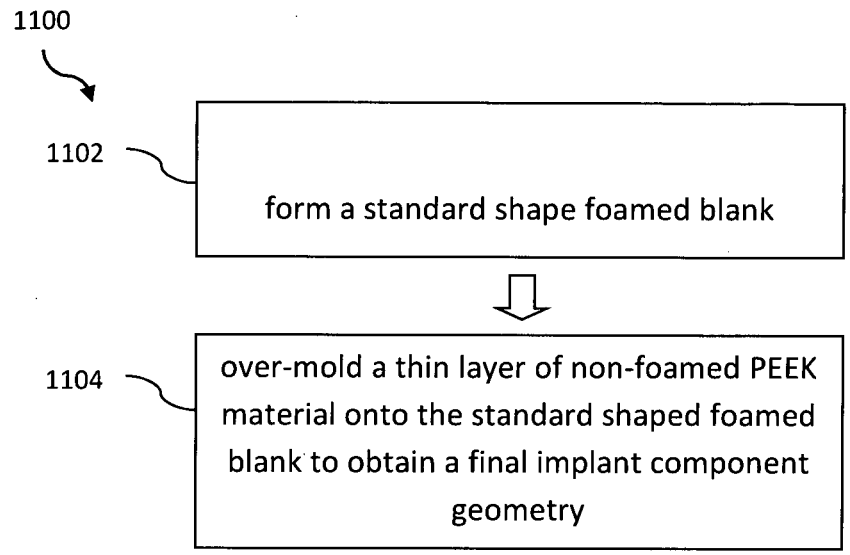
FIG. 11 is a flow chart of a process to create an implant of the present invention.

Now referring to FIG. 11, the invention provides a method 1100 for making an implant or component thereof that includes forming a standard shape foamed blank at step 1102, and over-molding a thin layer of non-foamed PEEK material onto the standard shaped foamed blank to obtain a final implant component geometry at step 1104.

Figure 12:
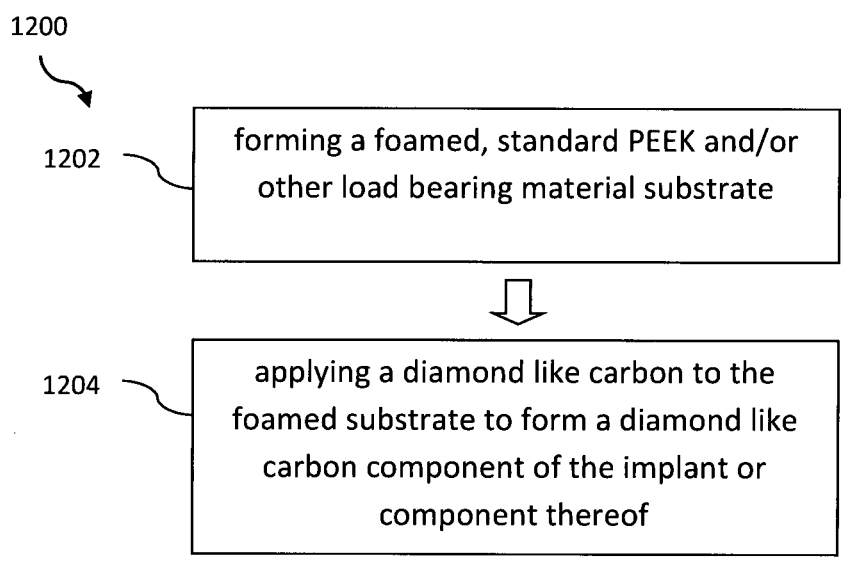
FIG. 12 is a flow chart of a variant of the process to create an implant of the present invention.

Now referring to FIG. 12, the invention provides a method 1200 for making an implant or component thereof comprising: forming a foamed, standard PEEK and/or other load bearing material substrate at step 1202, and applying a diamond like carbon to the foamed substrate to form a diamond like carbon component of the implant or component thereof at step 1204. Optionally, a bearing surface is also formed, the bearing surface comprising the diamond like coating, and the diamond like coating is outward of the load bearing material substrate. Also, a step of re-enforcing the load bearing material substrate with a carbon containing material is also included. The carbon containing material is a carbon fiber in one variant of the invention, although additional structurally re-enforcing materials, can also be used alone or in combination with the carbon fiber.

Figure 13:
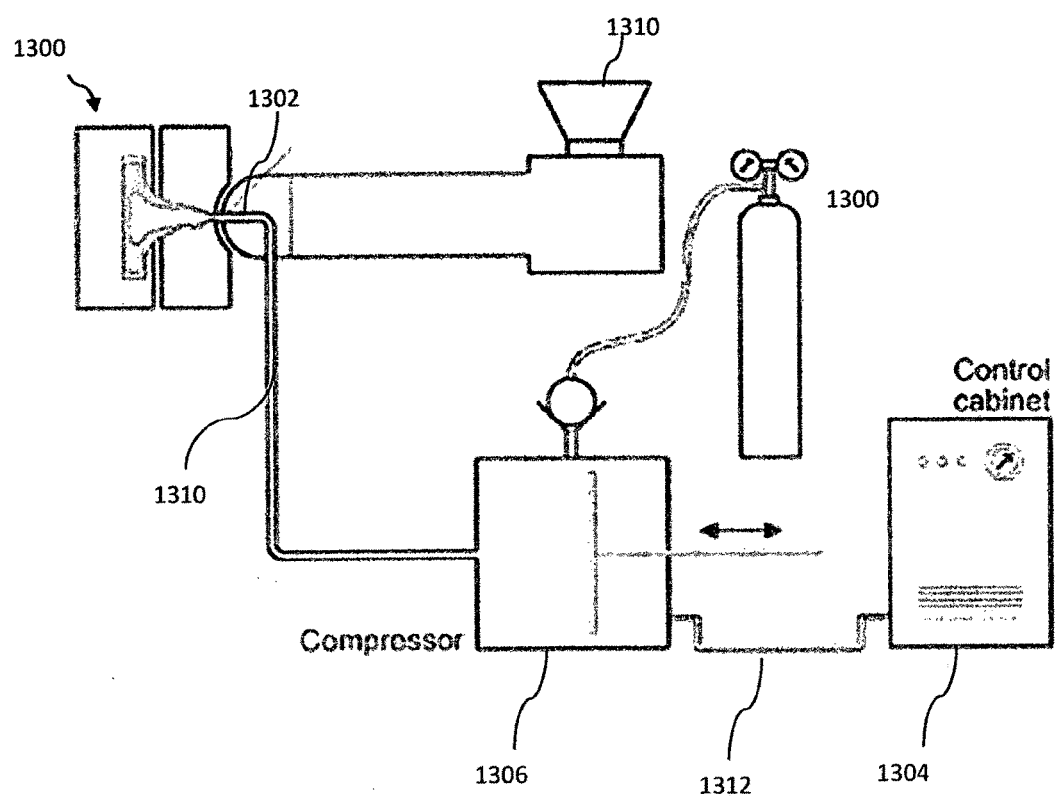
FIG. 13 is a variant of the system used to create an implant of the present invention.

Now referring to FIG. 13, system 1300 is used to create an implant of the present invention. System 1300 comprises system component 1310 which includes machine nozzle with gas-injection needle 1302. Control cabinet 1304 utilizes application software along with microprocessor controls, and memory controlling mechanical element and valve controls as well as consumables, and compressor 1306 which is connected to nitrogen pressure bottle 1308. Communication control cable 1312 links the compressor 1306 and other components of the system. Compressor 1304 is further connected to machine nozzle with gas-injection needle 1302 by conduit 1310.

Figure 14:
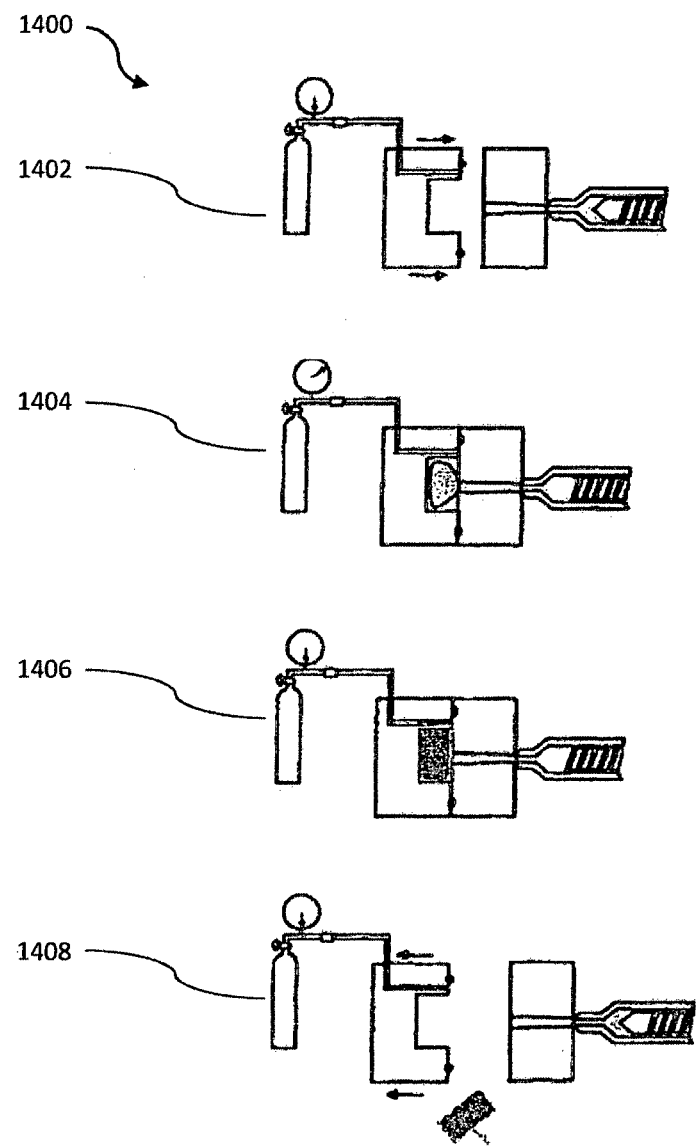
FIG. 14 is a variant of the method used to create an implant of the present invention.

Now referring to FIG. 14, method 1400 (which is executed via application software and mechanical controls to execute the method steps) is used to create an implant of the present invention, and is used in combination with the systems and/or other method steps described herein. Step 1402 illustrates the step (which via software and mechanical controls) closes the mold and builds up counter pressure. Step 1404 injects into the cavity under counter-pressure. Step 1406 executes the pressure relief and foaming operation. Step 1408 executes the mold opening and ejection operation.

In another variant, the methods and systems described herein are used to create a joint implant that includes a substantially hollow core (not shown). Surrounding some or all of the substantially hollow (or completely hollow) core is an outer layer mimicking the density of an exterior of a naturally occurring bone. An inner layer is also provided such that the inner layer is disposed beneath the outer layer and above the substantially hollow core, the inner layer being less dense than the outer layer, and the inner layer optionally mimicking the bone density of an interior portion of the naturally occurring bone. Optionally, the outer layer has a further layer thereon of DLC.

Figure 15:
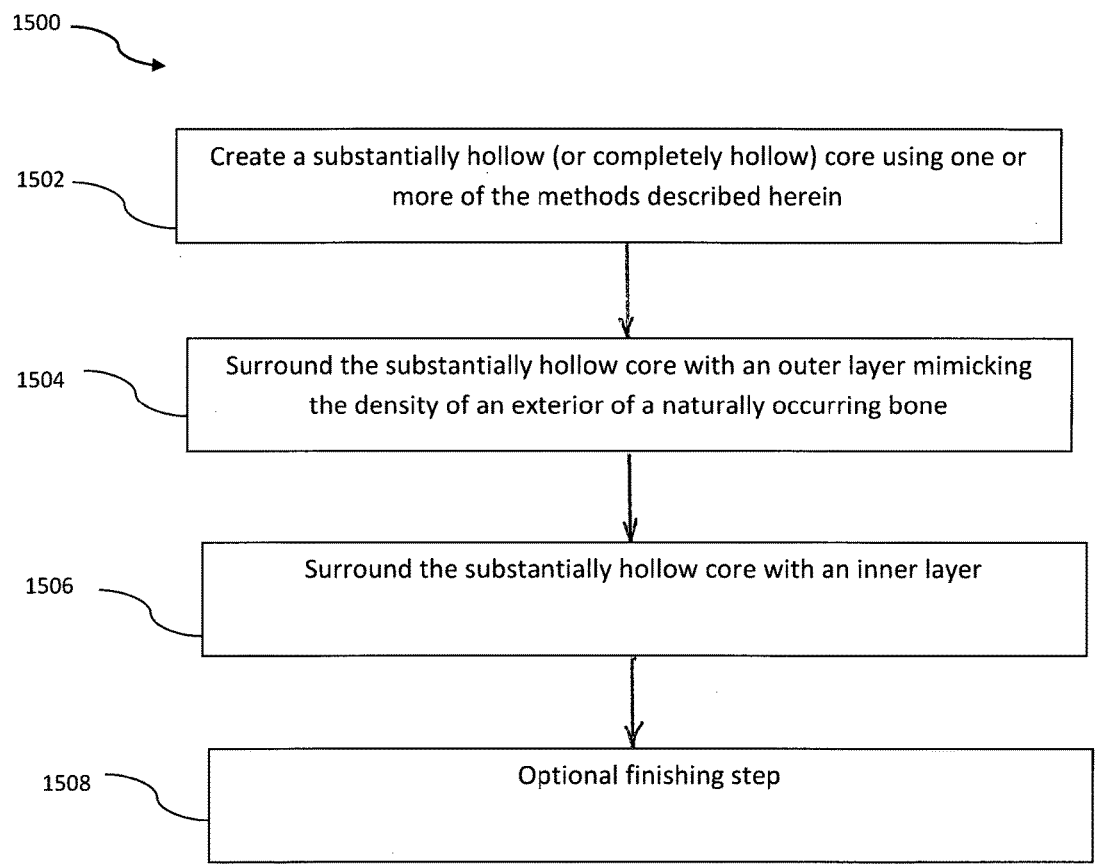
FIG. 15 illustrates a flow chart of a variant of the bone implant method for creating a plurality of joint implants using a system operated by operating software.

Now referring to FIG. 15, such a variant of the bone implant is created using a method 1500 for creating a plurality of joint implants using a system operated by operating software. Method 1500 includes a step 1502 for creating a substantially hollow (or completely hollow) core using one or more of the methods described herein. The next steps 1504, 1506 include surrounding the substantially hollow core with an outer layer mimicking the density of an exterior of a naturally occurring bone, and surrounding the substantially hollow core with an inner layer. The inner layer is disposed beneath the outer layer and above the substantially hollow core. The inner layer is less dense than the outer layer, but in a variant, may have the same density or a density other than the density of the outer layer. Optionally, the inner layer optionally mimics the bone density of an interior portion of the naturally occurring bone. Moreover, optional step 1508 includes one or more of the finishing steps described herein. In a variant, the bone prosthesis includes a hollow core with a bactericide gas enclosed inside during production and method step for effecting same. Diffusion of the gas is adjusted by modulating the crystallinity level of surface layers. It is appreciated, that in a variant, the implant created herein displays a "springiness" or elasticity close to or substantially close to that of the natural biomechanical state of naturally occurring bone, and has a modulus of elasticity very close or substantially close to that of bone in addition to excellent toughness (rigidity/wearability) and fatigue resistance.

Additional features and functionality of the invention are described in the claims appended hereto. Such claims are hereby incorporated in their entirety by reference thereto in this specification and should be considered as part of the application as filed.

Multiple variations and modifications are possible in the embodiments of the invention described here. Although certain illustrative embodiments of the invention have been shown and described here, a wide range of changes, modifications, and substitutions is contemplated in the foregoing disclosure. While the above description contains many specific details, these should not be construed as limitations on the scope of the invention, but rather exemplify one or another preferred embodiment thereof. In some instances, some features of the present invention may be employed without a corresponding use of the other features. Accordingly, it is appropriate that the foregoing description be construed broadly and understood as being illustrative only, the spirit and scope of the invention being limited only by the claims which ultimately issue in this application.

What is claimed is:

1. A method of processing an implant order, the method comprising the steps of:
   a. producing a variety of prosthesis pre-forms having a dense outer shell resembling cortical bone and a low density core or hollow center resembling cancellous bone, the pre-form sized so as to allow for optional secondary machining to a final desired shape without breaking through the dense outer shell into the low density core, the pre-forms thereby having a structure close to that of natural bone and a geometry suited to the needs of a class of patients;
   b. selecting the pre-form which best matches the needs of a particular patient or class of patients;
   c. as necessary, machining and finishing the pre-form to better conform to the particular patient or class of patients;
   d. sterilizing the pre-form; and
   e. packaging the sterilized pre-form for delivery of the pre-form to suit the needs of doctor and the particular patient or class of patients,
   wherein the prosthesis preforms are made using application algorithms for forming a standard shape foamed joint implant blank, and over-molding a thin layer of non-foamed PEEK material onto the standard shaped foamed blank to obtain a final implant component geometry, whereby the blank is at least partially encapsulated by the over-molded thin layer.

2. The method of claim 1, wherein the pre-form is formed of plastic material.

3. The method of claim 2, wherein the method comprises adding barium sulphate to the pre-form.

4. The method of claim 1, wherein the pre-form is formed of PEEK® plastic.

5. The method of claim 1, wherein the pre-form has a desired flexibility for the same external geometry.

6. The method of claim 1, wherein the pre-form has a desired density for the same external geometry.

7. The method of claim 1, wherein the pre-form has a desired stiffness for the same external geometry.

8. The method of claim 1, wherein the pre-form is formed to have a crystallised surface thereby allowing significant reductions in friction coefficient with a paired material.

9. The method of claim 1, wherein an anti-infection agent is injected within the pre-form.

10. The method of claim 1, wherein the anti-infection agents comprise silver ions.

11. The method of claim 1 further comprising adding barium sulphate to the implant or component thereof.

* * * * *